United States Patent
Horino

(10) Patent No.: US 6,730,309 B2
(45) Date of Patent: May 4, 2004

(54) SEBUM-ADSORBENT POWDER AND USE THEREOF

(75) Inventor: Masaakira Horino, Kanagawa (JP)

(73) Assignee: Miyoshi Kasei, Inc., Saitama (JP)

( * ) Notice: Subject to any disclaimer, the term of this patent is extended or adjusted under 35 U.S.C. 154(b) by 0 days.

(21) Appl. No.: 09/895,328

(22) Filed: Jul. 2, 2001

(65) Prior Publication Data

US 2002/0031534 A1 Mar. 14, 2002

(30) Foreign Application Priority Data

Jul. 6, 2000 (JP) ......................... 2000-204587

(51) Int. Cl.$^7$ ................. A61K 7/035; A61K 7/02; A61K 7/32; A61K 7/36; A61K 7/38
(52) U.S. Cl. .................. 424/401; 424/59; 424/76.2; 424/489; 424/490; 424/65; 424/67; 424/69; 424/602; 424/642; 514/782; 514/951
(58) Field of Search ............... 424/401, 59, 76.2, 424/489, 490, 65, 67, 69, 602, 642; 514/782, 951

(56) References Cited

U.S. PATENT DOCUMENTS 5,122,418 A * 6/1992 Nakane et al. ............... 424/401
6,004,584 A * 12/1999 Peterson et al. ............ 424/489

FOREIGN PATENT DOCUMENTS

| EP | 0 848 044 A1 | 6/1998 |
| JP | 9-227792 | 9/1997 |
| JP | 10-87420 | 4/1998 |
| JP | 10-204317 A | * 8/1998 |
| JP | 11-240819 | * 9/1999 |

OTHER PUBLICATIONS

JP 410204317A, Kuroda, Akihiro, Aug. 4, 1998, Cosmetic Powder and Cosmetic, abstract.*

JP 11–240819, Patent Abstracts of Japan, Japan Patent Office, Jul. 9, 1999, Taihei Chemical Industrial Co Ltd., See: entire document.*

XP–002222302 Database WPI, Section Ch, 199138; Derwent Publications Ltd., London, GB; AN 1991–276704.

* cited by examiner

Primary Examiner—Dwayne C. Jones
Assistant Examiner—Clinton Ostrup
(74) Attorney, Agent, or Firm—Westerman, Hattori, Daniels & Adrian, LLP

(57) ABSTRACT

A powder comprising a core powder, a hydroxyapatite layered directly on the core, and zinc layered directly on the hydroxyapatite, suitable for use in cosmetics. The powder has a light reflection curve similar to that of the surface of the skin so that it exhibits good skin feeling and is superior in long wear effect for makeup and antibacterial effect. The powder is also superior in adsorbing, solidifying, or congealing the sebum components or body odor components, and is useful as an effective component for a sebum-adsorbent agent, a body deodorant or the like in addition to cosmetics.

12 Claims, 6 Drawing Sheets

SPECTRAL REFLECTANCE, AMOUNT OF COATING : 0.04g/58cm$^2$
(THERE BEING NO UNDERLYING EMULSION)

SPECTRAL REFLECTANCE, AMOUNT OF COATING : 0.03g/58cm$^2$
(THERE BEING UNDERLYING EMULSION)

SEBUM-ADSORBENT POWDER AND USE THEREOF

BACKGROUND OF THE INVENTION

1. Field of the Invention

The present invention relates to a novel powder having a particularly excellent sebum-adsorbent property, and to a cosmetics, sebum-adsorbent agent, a body deodorant and the like, each employing the novel powder. More particularly, it relates to a powder comprising a base substance usable as a powder for cosmetics, a hydroxyapatite and a zinc oxide, preferably to a powder obtained on coating the surface of the substance with hydroxyapatite and fixing zinc oxide to the hydroxyapatite coating layer thereof, and particularly suitable for use in cosmetics, such as a sebum-adsorbent agent, or a body deodorant, or the like. It is possible to provide cosmetics, a sebum-adsorbent agent, a body deodorant and the like by the use of the powder in the present invention.

2. Description of the Related Art

The sebum secreted from the skin affords an emollient effect to the stratum corneum of the skin which keratinizes normally, prevents intrusion of toxic substance or bacteria from the outside, and controls the release of substances, such as water, out of the body. However, excess secretion of the sebum has a demerit that it may be a factor or so causing the makeup to come off which leads to some phenomena, for example, a "shiny" or "drab" appearance of the skin, or a "unevenness", "rumpling", or "disappearance" of the makeup itself, and the like caused by chronological changes in the cosmetic film that is coated on the skin, that may be due to the formation of peroxides by the oxygen contained in atmospheric air. Similar to photo-degradation of fats and oils, such formation of peroxides, if intruded into the skin, operates as irritants that may cause inflammation or a keratinization disorder, blemishes, or freckles on the skin. So, there is raised a demand for developing a technology for effectively removing sebum, wherein it takes account of safeness of the skin so as not to impose an excessive burden on the skin.

A variety of investigations have already been conducted from the viewpoint of improving long wear for makeup. For example, should highly moisture-absorbent or oil-absorbent substances, such as porous silica, calcium carbonate, magnesium carbonate, and crystalline cellulose, be mixed into cosmetics, moisture and sebum components on the skin become adsorbed, which leads to a shortage of skin emollient components and causes a dry skin feeling, and a tightness of skin or itchiness of skin. This phenomenon is most likely to occur with persons with dry skin and normal skin, in particular with persons living in an environment and the like (for example, persons working in an office) where perspiration (sweat) or sebum are not apt to be secreted. When used on oily skin, these substances have demerits, which are apt to present luster by the progress of the wet phenomenon due to excess sebum or oily components contained in the cosmetics, thus giving rise to a "shiny" look in the finished makeup.

Although cosmetics admixed with fluorine-processed powders have been proposed for improving the long wear for makeup, cosmetics making use of these powders, while not being wetted with sebum or perspiration, exhibits strong water- or oil-repellency thus causing the cosmetic film to be "rumpled" due to slipping of the powder on the skin thus impairing the makeup effect.

The cosmetics employing the powders treated with silicone are high in water repellency and also exhibit resistance against perspiration and moisture. However, the silicone oil, and the silicone oil or its derivative which is applied for surface treatment of the powder are low in oil resistance, basically due to the basic structure which the silicone oil has. Consequently, in the case of a person with an oily skin, the makeup may come off from the entire face due to excess secretion of sebum. On the other hand, in the case of a person with normal skin, the makeup may come off at the T- or V-zone of the face, so that it is difficult to prevent the makeup from coming off due to secretion of sebum.

A film forming polymer material may be utilized for improving long wear for makeup. As representative of this type of substance, an acryl-silicone based graft polymer has been proposed. This is produced and obtained by radical polymerization of a dimethyl polysiloxane composite which has a radical polymerizability at one terminal end of the molecular chain with a radical polymerization monomer composed essentially of an acrylate or a methacrylate, and forms a cosmetic film superior in water- and oil-repellency so that it is made practicable in a non-aqueous foundation. However, the cosmetics employing these polymers, from the viewpoint of enveloping the skin, leave many problems of a physiological aspect in the skin when taking into consideration the everyday biological activity on the surface of the skin. Moreover, in powder products in which the skin-forming capability cannot be used effectively, long wear is difficult to be improved.

There are also proposed a zinc oxide coated substance in which a base substance is coated with an amorphous zinc oxide, and there are reported a powder exhibiting good spreadability without detracting from the fatty acid-solidifying capability and an external agent for skin, using this powder (see Japanese Patent Kokai Publication JP-A-9-227792). However, the amount of adsorption of an oleic acid, which the zinc oxide coated substance exhibits, is approximately the same as that of the normal porous silica and is not particularly excellent in adsorption of the free fatty acids. Moreover, the amount of adsorption of an artificial sebum, which this coated substance exhibits, is lesser than the porous silica beads, and furthermore this coated substance takes approximately 30 minutes to solidify fatty acids, thus presenting difficulties in coping with the oily skin or ultra-oily skin.

On the other hand, there are reports of a composite, which is inclusive of one or more oxides and/or their hydroxides in the inter-layer of the clay mineral or an inter-layer metal inclusive composite adsorbing selectively only free fatty acids (see Japanese Patent Kokai Publication JP-A-10-87420). This material uses a water-swollen type of clay mineral and is produced by the reaction in the sol-state. As may be understood from the description of the Examples thereof, the reaction takes place in the diluted solution. Therefore, this method is costly in production per batch and is economically unmeritorious. Moreover, since the reaction occurs in the sol-state, the washing process is extremely time-consuming, when a regular filtering, washing, and drying process is used. The process is not only extremely time-consuming, but also the obtained product aggregates strongly, thereby not obtaining the result that is expected. In addition, a freeze-drying process is essential so that production becomes very expensive as another weak point. Although AL pillars are formed in the inter-layer of the clay mineral, the variations of content of intercalated oxide or hydroxide generates different states of pillars because of differences between lots of the clay mineral, it is usually difficult to obtain products in the same stable quality.

There is also a demand for the development of a substance (agent) for absorbing, adsorbing, solidifying, or congealing the body odor (smell), which is a body deodorant, which may or may not be comprised in cosmetics.

Under these above circumstances, there is a demand to develop a suitable skin-friendly powder, wherein the powder improves long wear for makeup, and can improve the demerits of the above prior substances, and can adsorb sebum, and also has antibacterial effect and body deodorant effect, in particular keep a cleanness and safeness of the skin by the cosmetics, by removing the free fatty acid (in particular the unsaturated fatty acid) and the secreted sebum.

SUMMARY OF THE INVENTION

Problem to be Solved by Invention

In view of the above, it is a problem to be solved by the present invention to provide a material suitable for use in cosmetics and the like, wherein the material specifically adsorbs free fatty acids (in particular unsaturated fatty acids), and also adsorbs, solidifies or congeals the secreted sebum, does not obstruct the skin physiology by making a solid film form, and has a light reflection curve (reflected light curve) similar to that of the surface of skin, and has a good skin feeling and is superior in long wear effect for makeup and antibacterial effect, and also has a deodorant effect.

Means to Solve Problem

The present inventors have conducted perseverant researches towards solving the above problem, and found that a powder comprising a base substance usable as a powder for cosmetics, a hydroxyapatite and a zinc oxide, preferably a coated substance, obtained on coating a hydroxyapatite on the surface of the substance and fixing a zinc oxide, more preferably a low crystalline zinc oxide (and/or an amorphous zinc oxide) to the coating layer, in particular the surface of that, of the hydroxyapatite, has such superior effects. It has also been found that the powder is superior in sebum-adsorbent property (in particular, the powder has high adsorbent properties with respect to unsaturated fatty acid and sebum, and also the time for solidifying unsaturated fatty acid and sebum is short), and the powder has an antibacterial effect and a property for adsorbing body odor components. The above variety of knowledge has led to the completion of the present invention.

That is, the present invention resides in a powder comprising a base substance usable as a powder for cosmetics, a hydroxyapatite and a zinc oxide, preferably a powder comprising a base substance usable as a powder for cosmetics, a hydroxyapatite coated on the surface of said substance and a zinc oxide fixed to the coating layer of said hydroxyapatite. Preferably, that is a powder obtained on coating the surface of the substance with hydroxyapatite to form a hydroxyapatite coating layer on the surface of the base substance and fixing a zinc oxide to the hydroxyapatite coating layer thereof. Moreover, the powder is suitable as a powder for cosmetics so that the powder can be applied to the cosmetics admixed with the powder, or to other fields of use. For example, since the powder has the property of adsorbing sebum components and the effect of deodorizing the body odor, the powder can be used for a sebum-adsorbent agent, a body deodorant and the like, therefore, the present invention contains these embodiments.

Now a sebum-adsorbent agent means an adsorbent agent for sebum, or an agent for adsorbing sebum.

Meanwhile, it suffices if the powder of the present invention comprises the aforementioned three components (that is the substance, the hydroxyapatite and the zinc oxide), and the powder of the present invention may compose other components or other structures, as far as the effect in the present invention is obtained or the object of the present invention is not obstructed. As a matter of course, these contents are contained in the powder of the present invention.

Meanwhile, as stated above, the sebum-adsorbent agent means a substance used for adsorbing, solidifying, or congealing the sebum of an animal, especially a human being. On the other hand, the body deodorant means a substance used for absorbing, solidifying, fixing, or deodorizing at least one of the components of disagreeable odor emitted through the skin of an animal, especially the skin of a human being, or from the epidermic cell (for example, due to perspiration (sweat) or effect of microorganisms and the like). In particular, the body deodorant may be used as the powder is mixed into the skin cosmetics or used as the powder mixed for deodorizing body odor separate from cosmetics.

In the present invention, the body odor (smell) components compose of a broad sense of body odor components which is emitted from the animal, especially the human body (see Seiichi Izaki, What is Body odor- its Cause and Prevention, Fragrance Journal, 1990-7, p.22 to 26 (1990); Yuuichi Yamamura, Body odor, 'Modern Dermatology 2B' Whole Body and Skin 2, edited by Yuuichi Yamamura, Jun Kukita, Eishun Sano, Makoto Seiji, published by NAKAYAMA SHOTEN, Tokyo, 1981, 163).

BRIEF DESCRIPTION OF THE DRAWINGS

FIG. 1 shows the measured results of the spectral reflectance as measured by a spectrophotometer for comparing the transparent feeling (transparency) in Example 2, where the sample: ● denotes the skin (devoid of samples), ■ denotes the sericite and ▲ denotes the inventive substance (Example 1).

FIG. 1(a) shows direct coating on the skin in an amount of 0.04 g/58 cm$^2$ for the sample and FIG. 1(b) shows coating of the emulsion on the underlying ground in an amount of 0.03 g/58 cm$^2$ for the sample.

FIG. 2 is a photo of the state of the skin (face) five hours after coating the face with the powder, as taken by a digital camera in Example 2 (comparison of the effect by use), under a light.

FIG. 2(a) shows the skin and right face and FIG. 2(b) shows the inventive substance (Example 1), left face.

FIG. 3 is a video microscope photo (magnification factor; ×200) in the Example 2 (comparison of the effect by the use) as observed after lapse of five hours after coating the face with the powder.

FIG. 3(a) shows the skin, right face and FIG. 3(b) shows the inventive substance (Example 1), left face.

FIG. 4 shows a photo taken by the digital camera in Example 6, with the photo taken under the light near the window for showing the state of the skin (face) after lapse of five hours after coating the face with the powder foundation.

FIG. 4(a) shows the inventive substance (Example 3), right face, near the window;

FIG. 4(b) shows the product of the Comparative Example 1 for showing the left face near the window;

FIG. 4(c) shows the use of the inventive substance (Example 3), right face, under the light;

FIG. 4(d) shows the use of a product of the Comparative Example 1, left face, under the light;

FIG. 4(e) shows a photo of FIGS. 4(c) and 4(d) simultaneously, with the left side face on the photo (right face) being coated with the inventive substance.

FIG. 5 is a video microscope picture in Example 6 (magnification factor, ×200) as observed five hours after coating the surface with the powder.

FIG. 5(a) shows an inventive substance and FIG. 5(b) shows a product of the Comparative Example 1.

PREFERRED EMBODIMENTS OF THE INVENTION

Figure 1:
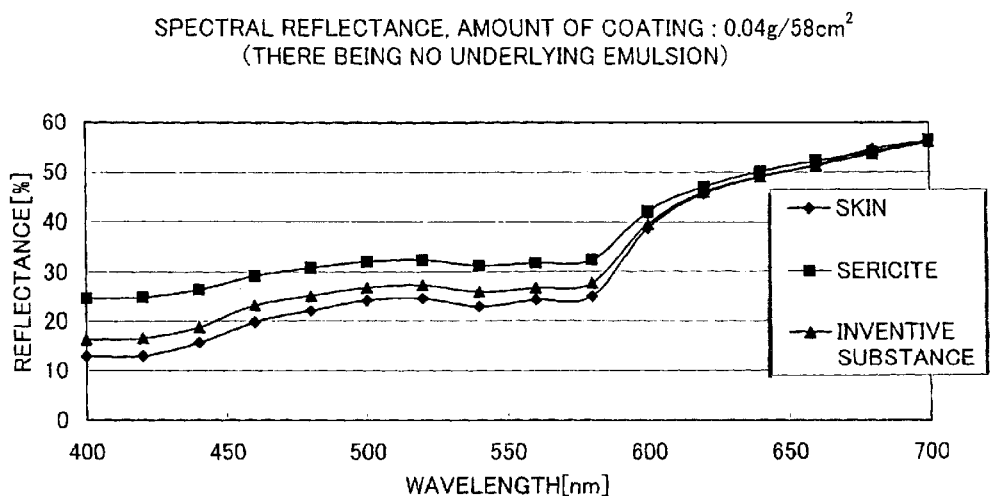
FIG. 1
Figure 1:
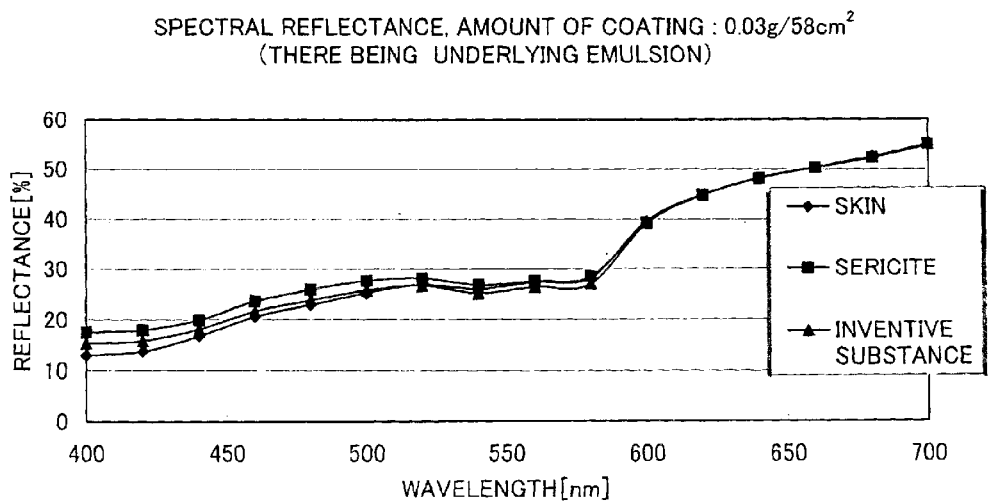

In the following, a preferred embodiment of the present invention is explained in detail.

The powder of the present invention comprises a base substance usable as a powder for cosmetics, a hydroxyapatite and a zinc oxide. Preferably, the powder comprising these components and which are in the form of a coated substance is cited. The following explanation is centered about this coated substance. The powder of the present invention contains this coated substance only by way of an example, and therefore is not limited thereto.

Coated Substance (Composite Material) of the Present Invention

The coated substance of the present invention has a basic structure which is comprised of a base substance, a hydroxyapatite coating layer on the surface of the base substance, and a zinc oxide fixed to the coating layer thereof, preferably to its surface. More preferably, low crystalline zinc oxide, amorphous zinc oxide or a mixture thereof is used as a zinc oxide, and is fixed to the hydroxyapatite layer for forming the coated substance in the present invention highly useful as cosmetics. The substance can be employed for a powder usable as cosmetics, both inorganic and organic, and may be used in the form of variety of composite powders, such as inorganic-inorganic powders, organic-organic powders, inorganic-organic powders, and the like. Among inorganic powders, there are clay minerals, metal oxides, metal hydroxides and composite materials comprising these materials, and the composite material(s) of one or more these inorganic material(s) with one or more organic material(s). As the organic powders, those usable for the substance of variety of cosmetics may be used. As a matter of course, natural products or synthetic clay minerals may be contained in the clay minerals. It is also possible to use a composite material of the organic and inorganic powders, that is, the organic-inorganic composite powders. In the case of using them in the cosmetics and the like, one or more of these powders may, of course, be used.

There is no particular limitation to the particle shape. For example, there may be a variety of shapes, such as lamellar shape, scale-like shape, plate-like shape, spherical shape, spindle shape, X-shape, starfish-like shape, ribbon-like shape, hemispherical shape, needle-like shape, bar-like shape and the like. The lamellar, scale-like, plate-like or bar-like shape is particularly preferred in that it is ready to produce the same light reflection curve as that obtained on the surface of skin.

The size of the particle in the powder used for the base substance, expressed as mean particle size, is preferably on the order of 0.1 to 600 μm, more preferably on the order of 0.3 to 140 μm, moreover preferably on the order of 1 to 80 μm and most preferably on the order of 2 to 50 μm.

In the present invention, the clay minerals used in the base substance, may be inclusive of synthetic products, and may be enumerated by kaolins, such as kaolionite, dekkite, nacrite, halloysite, antigorite, chrysotile and the like, smectites, such as pyrophyllite, montmorillonite, nontronite, sabonite, hectorite, bentonite and the like, illites, such as sericite, white mica, black mica, lithia mica, gold mica, synthetic mica, synthetic sericite and the like, silicates, such as calcium silicate, magnesium silicate, magnesium aluminum silicate and the like, magnesium silicates, such as talc, serpentine and the like, natural and synthetic zeolite, tourmaline and the like. If metal oxides are used as the base substance, single component powder, such as silica, alumina, titanium oxide, cerium oxide and the like, bismuth oxychloride, barium sulfate and the like, may be used. In particular, plate-like shaped or scale-like (scalar) shaped products are desirable. Moreover, the form of composite material may be used. The composite oxides may be enumerated by multi-layered composite material, such as silica-titanium dioxide, silica-zinc oxide, silica-titanium dioxide-silica, silica-cerium oxide-silica, silica-zinc oxide-silica and the like, pearl pigments, such as titanium mica, colored titanium mica, titanium dioxide-barium sulfate, titanium dioxide-talc, zinc oxide-mica, zinc oxide-talc, bismuth oxychloride-mica and the like, the surface of these pearl pigments treated with aluminum hydroxide, aluminum oxide, magnesium hydroxide, magnesium oxide, silica, barium sulfate or the like, and hard capsules, such as titanium dioxide encapsulating PMMA, zinc oxide encapsulating PMMA, cerium oxide encapsulating PMMA and the like.

Among the organic powder used as a base substance, there are a variety of powders usable for cosmetics, such as nylon powders, polyethylene powders, polypropylene powders, polystyrene powders, vinyl acetate powders, polymethacrylic acid ester powders, polyacrylonitrile powders, cellulose powders and the like. The organic-inorganic composite powders may be enumerated by polyethylene-zinc oxide, polyethylene-titanium dioxide, polyethylene-aluminum hydroxide, polyethylene-aluminum hydroxide-PMMA and the like. If the organic-organic composite powders are used, nylon-cellulose may be used.

There is no particular limitation to the hydroxyapatite used in the present invention. It is defined as calcium phosphate, with Ca/P=0.5 to 2.0 (in molar ratio), having an apatite structure (see Fragrance Journal, p144 to p148, 1999 January). Such calcium phosphate may be used in the present invention.

The hydroxyapatite, that is coated on the surface of base substance, has the action of specifically adsorbing free fatty acids, in particular unsaturated fatty acids. It may be presumed that this free fatty acid, somewhat exhibiting sebum-solidifying capability, operates as a factor responsible for causing makeup to come off due to the action of specifically lowering the melting point of the sebum. The hydroxyapatite adsorbs free fatty acid secreted from the skin and prevents the makeup from coming off due to the lowering of the melting point of the sebum. The hydroxyapatite also plays the role of keeping the skin clean by the adsorptive action of peroxides generated due to oxidation of sebum secreted from the skin.

The hydroxyapatite coating that is coated on the surface of the base substance increases its crystallinity by heat treatment, with the crystallinity being higher, a higher heat treatment temperature being necessary. However, since the amount of the fatty acid adsorbed is inversely correlated with the heat treatment temperature, it is more desirable not to apply heat treatment.

Although there is no limitation to the hydroxyapatite used in the present invention, as described above, $Ca_5(PO_4)_3(OH)$, $Ca_{10}(PO_4)_6(OH)_2$, $Ca_4(PO_4)_2O$, $Ca_{10}(PO_4)_6F_2$, $Ca_3(PO_4)_2$ and the like are cited preferable in view of safety.

The amount of hydroxyapatite used for coating is preferably on the order of 2 to 50 wt %, more preferably on the order of 5 to 30 wt % and most preferably on the order of 10 to 20 wt % based on the weight of total composition of powder, in particular, the total weight of the base substance, the hydroxyapatite and zinc oxide. The coating amount less than 2% is insufficient to keep the skin clean due to the excessively small amount of the adsorption. If the coating amount exceeds 50 wt %, the amount of adsorption cannot be expected to be increased in proportion to the amount used for coating. Moreover, the slipperiness (lubricant property) on the skin is undesirably lowered. Although there is no limitation to the thickness of the coating layer, it is preferably on the order of 0.05 to 4 $\mu$m and more preferably on the order of 0.1 to 2 $\mu$m.

After coating the surface of the base substance with a hydroxyapatite, zinc oxide is fixed to the hydroxyapatite coating layer, for example, to its surface. As a zinc oxide for fixing, since zinc oxide having high crystallinity is low in both free fatty acid-adsorbent properties and sebum solidifying capability for solidifying the sebum, it is desirable to use low crystalline zinc oxide, amorphous zinc oxide or mixtures thereof. The particle size, expressed as mean particle size, is preferably on the order of 0.01 to 1 $\mu$m, more preferably on the order of 0.03 to 0.5 $\mu$m, and most preferably on the order of 0.05 to 0.1 $\mu$m.

Meanwhile, "low crystalline", in the low crystalline zinc oxide, means the state in which crystalline planes are not arrayed neatly in numerous random orientations of small-sized crystals. The X-ray diffraction peak width is determined by the variable orientations (arraying states) of individual micro-crystallites and the crystalline size. In the case of the large crystalline size, light scattering is small, whereas, in the case of the small crystalline size, the peak width is broad. The crystalline size may be obtained from the following Scherrer's equation:

Scherrer's Equation $$L=(K\lambda)/(\beta_0 \cos \theta_B)$$

where

L=crystalline size in Å
K=constant (=1.0)
$\lambda$=wavelength of X-rays (=1.5406 Å)
$\theta_B$=Bragg's angle
$\beta_0=(\beta_E^2-\beta_I^2)^{1/2}$
$\beta_E$=apparent half value width (measured value)
$\beta_I$=constant of a mechanical device (=1.75×10$^{-3}$ rad.)

Although the above equation is lowered in reliability when the numerical value exceeds 1000 Å, it may be seen that the crystalline size of the low crystalline zinc oxide is evidently small in crystalline size as compared to that of the crystalline zinc oxide.

The result of calculating the crystalline size L of zinc oxide is as follows:

| samples | H | K | L | 2THETA/DEG. | HALF WIDTH/DEG. | L (Å) |
|---|---|---|---|---|---|---|
| crystalline zinc oxide | 1 | 0 | 0 | 10.83 | 0.12 | 1562.5 |
| | 0 | 0 | 2 | 25.86 | 0.13 | 1091.1 |
| low crystalline zinc oxide | 1 | 0 | 0 | 10.79 | 0.46 | 196.3 |
| | 0 | 0 | 2 | 25.84 | 0.20 | 541.4 |

For analysis, the (100) plane and the (002) plane of zinc oxide are used. The crystalline size represents the size in a direction perpendicular to these planes. In the low crystalline zinc oxide, the crystalline size is larger in the (002) direction than in the (100) direction. In the crystalline zinc oxide, this relationship is reversed, such that growth occurs significantly in the (100) direction.

If the crystalline zinc oxide and the low crystalline zinc oxide are compared to each other, it may be seen that the crystalline zinc oxide has a value exceeding 1000 Å in crystalline size, whereas the low crystalline zinc oxide obviously has a crystalline size not larger than 1000 Å, thus being small in crystalline size.

As the low crystalline zinc oxide used in the present invention, the crystalline size of zinc oxide, expressed aforementioned crystalline size, preferably 100 nm (1000 Å) at most (at the longest), more preferably 2 to 100 nm (20 to 1000 Å) and most preferably 3 to 100 nm (30 to 1000 Å)

The "amorphous", in the amorphous zinc oxide, is defined as being in the solid state in which the crystal lattice (periodic array of atoms) is hardly noticed or as being a solid which fails to give an X-ray diffraction image even if there exists certain periodic array of atoms Although the sebum composition differs with the sex and with age, with the result done by the researches of SHISEIDO KK, in the case of a female, the sebum comprise free fatty acid on the order of 7 to 13%, squalene on the order of 11 to 17%, wax on the order of 14 to 17%, triglyceride on the order of 47 to 55%, diglyceride on the order of 3 to 5%, monoglyceride on the order of 0.7 to 1.2%, stearin esters on the order of 1.4 to 1.5% and free stearins on the order of 1.4 to 1.5%. Therefore, if approximately 7 to 13% of free fatty acids in the sebum composition only is adsorbed, many other sebum components remains on the skin, such that the prevention of the makeup from coming off is done insufficiently, and hence it is necessary to adsorb, solidify or congeal other secreted sebum components to prevent the sebum from being fluidized.

The powder of the present invention has particularly superior features in specifically adsorbing free fatty acid in the sebum composition and also prevents the melting point of the skin from being lowered, and in exhibiting higher sebum-solidifying capability with higher capability of adsorbing fatty acid (fatty acid-adsorbing capability), through the interaction between the action of adsorbing the other sebum components, such as diglyceride or triglyceride and ester, and the sebum-solidifying capability. Moreover, the powder of the present invention can keep the skin clean because it has properties of forming a strong cosmetic film that prevents the makeup from coming off and adsorbing the peroxides generated by oxidation of sebum, and having antibacterial activities. The cosmetic film obtained according to the present invention is superior in transparency, exhibits the same pattern as that of the skin's spectroscopic curve, and prohibits non-transparency or the whitish powder floating on the makeup finish. Moreover, its adherency to the skin and skin feeling are given in so far as the cosmetic effect is concerned, while the aesthetic feel is also equivalent to that of the scale-like powders routinely used in the cosmetics.

The amount of zinc oxide used in the powder of the present invention is preferably on the order of (approximately) 2 to 8 wt %, more preferably on the order of (approximately) 3 to 7 wt % and most preferably on the order of (approximately) 4 to 6 wt % based on the total composition (weight) of the powder, in particular the total weight of the base substance, the hydroxyapatite and the zinc oxide involved. The amount of zinc oxide less than 2 wt % or exceeding 8 wt % are both undesirable in that the sebum-solidifying capability is markedly lowered in the former case, whilst the sebum-solidifying capability tends to be lowered due to interaction in the latter case.

The coated powders of the present invention can be produced without particular difficulties by, for example, the following method:

A liquid comprising a base substance dispersed therein is added to calcium acetate and is heated to 85° C. and admixed with a mixed solution of sodium hydroxide and disodium hydrogenphosphate ($Na_2HPO_4$). The pH value then is adjusted to approximately 9 to 10. The resultant product then is added to a sodium hydroxide solution and the pH value is adjusted to approximately 11 to 12. The resultant product is kept at approximately 85° C. and cured. After the end of curing, the solution is cooled and set at a temperature of approximately 60° C. When the temperature is at 60° C., the reaction mixture is adjusted to the pH value of approximately 12 by adding a 5N sodium hydroxide solution thereto. As the pH value is adjusted to and kept at approximately 12, a 1M zinc chloride solution and a 5N sodium hydroxide solution are dripped into the reaction mixture simultaneously. After that, the reaction mixture is cooled, filtered and washed with water repeatedly. The reaction product is dried at 120° C. for 16 hours or so and pulverized to obtain a coated powder of the present invention. The coated substance of the present invention, obtained as described above, specifically adsorbs the free fatty acids while simultaneously adsorbing and solidifying other sebum components, while maintaining its aesthetic feel, and is superior in the long wear effect for makeup, skin cleanliness (cleanness of the skin) and skin feeling, and in antibacterial properties.

Thus, the coated substance of the present invention is suited as a starting material for preparations of cosmetics and drugs. In particular, it is useful as a starting material for cosmetics since it is excellent in long wear for makeup and in antibacterial properties, while maintaining skin cleanliness and skin feeling. Moreover, it may be used as a sebum-adsorbent agent or as a body deodorant.

Cosmetics

The cosmetics of the present invention have features in that it comprises the coated substance (powder) of the present invention as described above. The cosmetics of the present invention can be applied to any agent form known for ordinary cosmetics, in particular it is not limited. These cosmetics may be applied to, for example, basic cosmetics, such as cream, emulsion, lotion, sun-cam lotion and the like, point makeup agents, such as under-makeup, foundation, eye-shadow, lip cream, rouge brusher, lip gloss, lip color and the like, powder products, such as talcum powder, caramine lotion, baby powder, body powder, deodorant powder, fragrance powder, face powder and the like, and hair treatment products. The cosmetics of the present invention can also be applied to wet tissues, oil removing sheets or makeup removing agents and the like. In particular, the cosmetics of the present invention can be more desirably enumerated by makeup cosmetics, basic cosmetics and sweat controlling cosmetics (especially deodorant cosmetics and the like).

The reason is that the coated substance of the present invention exhibits a deodorant effect and antibacterial properties and, when the coated substance of the present invention is used as cosmetics, it exhibits a high adsorptive power for free fatty acids and sebum components, while being superior in long wear for makeup and skin feeling.

When the coated powders of the present invention is composed in cosmetics, there is no particular limitation to the amount of mixing in the cosmetics since it may be suitably selected depending on the type of the cosmetics. In general, preferably on the order of 0.01 to 50 wt %, more preferably on the order of 0.05 to 30 wt % and most preferably on the order of 0.1 to 20 wt % may be mixed in the entire cosmetics.

In addition to the coated substance of the present invention, those components used in routine cosmetics may be used. These components may be enumerated by hydrocarbons, such as vaseline, micro-crystalline wax, ceresin, squalane, fluid paraffin and the like, higher alcohol, such as cetanol, stearyl alcohol, olein alcohol and the like, fatty acids, such as stearic acid, palmitic acid, behenic acid and the like, triglycerides, such as beef tallow, olive oil and the like, esters such as myristic acid octyl dodecyl, dimethyl octanoic acid hexyldecyl, myristic acid isopropyl and the like, polyhydric alcohols, such as glycerine, 1,3-butylene glycol and the like, nonionic surfactants, anionic surfactants, amphoteric surfactants, cationic surfactants, ethanol, thickeners, such as carboxy vinyl polymer, carboxy methyl cellulose sodium and the like, antiseptics, UV light absorbents, antioxidants, dyes and powders.

Sebum-Adsorbent Agent

The present invention contains a sebum-adsorbent agent. In particular, the present invention may be applied with the intention or the power of adsorbing, solidifying or congealing the sebum components of a human being. Therefore, the sebum-adsorbent agent also encompasses the aforementioned cosmetics. The product of the present invention may also be used as a sweat controlling agent in addition to the cosmetics. The content of the powder to be mixed to the sebum-adsorbent agent can be selected suitably. If the product of present invention is used for objects other than cosmetics, the amount of mixing used in the cosmetics can be used as reference values.

Body Deodorant

Usually, the body deodorant can be mixed into cosmetics for adsorbing, solidifying or congealing the body odor (smell) and the like, that is undesirable odor components emitted by perspiration or microorganisms through the skin of animals, in particular the skin of human being, and can decrease the odor. According to the present invention, a body deodorant is a substance (agent) used for adsorbing or solidifying at least one odor component emitted in particular from the human body through the skin, and the like, for reducing the odor (smell). The use thereof to the cosmetics is as described above. It can be affected by using the formulation customarily used or known as deodorant or antibromic agent (see Yoshihiro Ohhata, Tendency and Task of Recent Body Deodorant Products, Fragrance Journal, 1990-7, p-61 to 69, 1990). The amount of mixing of the powder of the present invention can be selected suitably depending on the species of agent form and the like. Usually, the amount of mixing, which is shown in the above-described cosmetics is referred.

This application is based on the Japanese Patent Application Ser. No.2000-204587, field on Jul. 6, 2000, which is incorporated herein by reference in its entirety.

EXAMPLES

The present invention is explained in detail by referring to the following Examples and Comparative Examples.

Example 1

Preparation of Powder 95 g of sericite (mean particle size: 8 μm, plate crystal) were dispersed in 1000 ml of purified water in the reaction vessel. To the resultant liquid dispersion 32.4 g of calcium acetate were added and the resultant mixture was heated to 85° C. When the temperature is 85° C., a solution obtained on dissolving 6.0 g of sodium hydroxide and 15.9 g of disodium hydrogenphosphate in 350 ml of purified water was added to the heated mixture to adjust the pH value of the solution to 9.4. A solution obtained on dissolving 1.35 g of sodium hydroxide in 200 ml of purified water was then added to the mixture to adjust the pH value thereof to 11.4. The reaction mixture was subjected to reaction and curing for one hour. When the curing was finished, the reaction mixture was cooled to 60° C., and 75 ml of 1M zinc chloride was added drop wise thereto, as the pH value was kept at 12, using a 1M zinc chloride solution and 5N sodium hydroxide solution. At the end of the dripping, the reaction mixture was cooled, filtered and washed with water repeatedly. The reaction product was dried at 120° C. for 16 hours and pulverized to obtain a coated product (powder) of the present invention.

Example 2

Various Evaluation Tests for Powder
Test Method
A. Amounts of Adsorption of Various Fats and Oils and Artificial Sebum 5.0 g of a sample was weighed out precisely in a 300 ml beaker and, as an example of fats and oils, 50.0 g of the artificial sebum were weighed out precisely. In this time, if the artificial sebum is in the semi-solid state, it is heated to hive a complete solution, and then weighed out precisely. Each weighed sample was agitated vigorously for 30 minutes by a magnetic stirrer and placed stationary for 18 hours in a constant temperature chamber at 32° C. The samples were taken out from the constant temperature chamber and added to with 100 ml of petroleum ether. After the resultant product was agitated for 30 minutes, the product was filtered. This operation was repeated thrice and the resultant product was dried at 80° C. The resultant sample was weighed out precisely and was held at 500° C. for four hours and fired and the amount of adsorption was obtained from the decreased amount of the sample.

The amount of adsorption of the artificial sebum in a mixed system of the artificial sebum and the pseudo-perspiration composition was measured in the same way as the above description by using 5.0 g of the sample to the equation: Perspiration composition (g)/Artificial sebum (g)= 20/80 to 80/20.
B. Fatty Acid-solidifying Capability (Solidification Starting Time)

3.6 g of oleic acid was precisely weighed out in a 50 ml beaker into which 1.0 g of the sample was charged and vigorously stirred and homogeneously mixed for ten minutes with a magnetic stirrer. The liquid mixture was set stationary and the beaker charged with the sample was tilted (inclined) and fluidized. When the beaker was returned to the original stationary set state, the time during which the deformed shape on tilting was maintained was used as the solidifying capability (solidification starting time).
C. Transparency by Spectroscopic Photometer (Skin Feeling)

An area 58 cm$^2$ was fixed, using the arm of a forearm flexed portion and 0.04 g of the sample was uniformly coated using a urethane puff. The reflectance of the spectroscopic reflected light was measured. The underlying ground was coated with an emulsion and 0.03 g/58 cm$^2$ of the sample was coated on the same site to effect similar measurement (using a spectroscopic photometer SZ-Σ90 manufactured by NIPPON DENSHI KK).

D. Coefficient of Dynamic Friction (Dynamic Frictional Coefficient)

Using a friction sensory tester KES-SE manufactured by KATOTEC KK., the pressure sensitive portion and the powder surface were reciprocated three times, the coefficient of dynamic friction (the dynamic frictional coefficient) was measured.
E. Amount of Absorption of Oil 5.0 g of the sample was taken on a glass plate and squalane as a component similar to sebum was applied drop wise thereto. The reaction mass was kneaded homogeneously with a spatula until the sample was collected as a sole mass. At this point, as an end point, the amount of squalane dripped until this time was used as the amount of absorption of oil of the sample (ml/100 g)
Evaluation Test as to a Variety of Powders
(1) Amount of absorption of oil, specific surface, amount of adsorption of oleic acid, amount of adsorption of artificial sebum and fatty acid-solidifying (oleic acid solidification starting time).

The measured results are shown in the following Table 1.

TABLE 1

| samples | amount of absorption of oil ml/100 g | specific surface m/g | amount of adsorption of oleic acid mg/g | amount of adsorption of artificial sebum mg/g | time of solidification |
|---|---|---|---|---|---|
| sericite | 87 | 7.8 | 7.3 | | x |
| crystalline zinc oxide | 92 | 9.3 | 17.4 | | 89 min |
| low crystalline zinc oxide | 241 | 61.9 | 418.0 | | 33 sec |
| hydroxy-apatite | 223 | 63.1 | 59.1 | | x |
| smectite | 62 | 228.3 | 137.9 | | x |
| hectorite | 49 | 340.3 | 175.0 | | x |
| magnesium aluminum silicate | 420 | 357.7 | 292.0 | | x |
| porous spherical silica | 147 | 305.4 | 71.5 | 65.3 | x |
| titanium dioxide (rutile type) | 48 | 12.0 | 0.7 | | x |
| Japanese Patent Kokai Publication JP-A-9-227792 | 95 | 8.7 | 73.3 | 40.0 | 32 min |
| inventive substance (Example 1) | 130 | 19.9 | 229.0 | 204.6 | 8 min | x: not solidified

If evaluation is made from the results of the amount of absorption of oil, specific surface, amount of adsorption of oleic acid, amount of adsorption of artificial sebum and fatty acid-solidifying power (time of solidification), the inventive substance (powder of the Example 1) has an amount of oil absorption (amount of absorption of oil) which is slightly higher than the amount of oil absorption of 90 to 120 of the powder mixed as a main filler, a high amount of oleic acid adsorption (amount of adsorption of oleic acid), a high amount of oleic acid adsorption per unit specific surface and a high amount of artificial sebum adsorption (amount of adsorption of artificial sebum) and a shorter oleic acid solidification starting time. Moreover, the in inventive substance is evidently superior to the zinc oxide coated substance as a prior product (see Japanese Patent Kokai Publication JP-A-9-227792) in the amount of absorption of oleic acid, the amount of adsorption of sebum, the amount of adsorption of artificial sebum and the solidification starting time.

(2) Amount of Adsorption of each Fats and Oils for the Inventive Substance

The amount of each fats and oils adsorbed for the inventive substance was measured and the results are shown in the following Table 2:

TABLE 2

| fats and oils | amount of adsorption mg/g |
|---|---|
| glycerine tri-2-ethyl hexanoate | 18.4 |
| glyceryl dioleate | 35.2 |
| O.D.O. manufactured by NISSHIN SEIYU KK | 24.4 |
| octyl dodecyl oleate | 20.9 |
| methyl polysiloxane* | 11.8 |
| isostearic acid | 42.5 |
| oleic acid | 229.0 |
| squalene | 24.0 |

*50 centistokes

It may be seen from the measured results of the amount of adsorption, that the inventive substance specifically adsorbs free fatty acids and in particular unsaturated fatty acid selectively, and that the inventive substance also exhibits an adsorptive power for saturated fatty acids, triglycerides, diglycerides, esters and the like, thus being superior in the sebum adsorptive power.

(3) Amount of the Adsorption in the Mixed System of the Artificial Sebum (Manufactured by MIYOSHI KASEI KK) and the Pseudo-perspiration (Sweat) Components for the Inventive Substance The amount of adsorption of the artificial sebum, with respect to the inventive substance (Example 1), was measured and a comparison was made based on the compositions. The results are shown in the following Table 3:

TABLE 3

| pseudo-perspiration components g | artificial sebum g | amount of adsorption of artificial sebum mg/g |
|---|---|---|
| 20 | 80 | 220.9 |
| 50 | 50 | 236.6 |
| 80 | 20 | 241.1 |

Meanwhile, the test was conducted using 5.0 g of the sample.

Composition of Pseudo-perspiration (Sweat) Components

The pseudo-perspiration (sweat) components are in the composition of: 98% of purified water, 0.5% of urea, 1.0% of sodium chloride and 0.5% of glucose.

On the human skin, there are 100 to 150 perspiration (sweat) glands on an average per 1 $cm^2$. The perspiration (sweat) glands are roughly divided into eccrinic (eccrine) glands and apocrine glands. If the perspiration from both of these glands is summed together, the secreted amount (the amount of secretion) in the still state is 300 to 500 cc per day and in an ordinary life environment is 2000 to 3000 cc per day. The face subjected to makeup is not an exception. What is crucial in actuality is not the amount of the moisture dissipated and evaporated from the skin surface (the surface of skin) but the correlation between the perspiration (sweat) retained on the skin, secreted sebum and the makeup film. It is seen that, in the perspiration to sebum mixed system, the amount of adsorption of the artificial sebum (the adsorbed amount of the artificial sebum) is not lowered even if a large amount of perspiration is secreted, but rather the adsorbed amount (the amount of adsorption) is increased, there being no obstruction of the adsorbed amount of the sebum (the amount of sebum adsorption) by the perspiration. It is also seen from the experiments on the secreted amount equal to 20 times as much as the sample that a uniform solid film free of fluidity, such as w/o, is produced in the range of the sebum to perspiration ratio of 8/2 to 5/5. In actuality, the pigments and powders in the makeup cosmetics are captured in the solid film. In addition, the free fatty acid in the sebum is presumably adsorbed in the inventive substance to suppress the lowering of the sebum to form a solid film with more solid content and a stronger cosmetic film to assure superior long wear effect for makeup.

(4) Comparison of Transparent Feeling (Transparency)

The spectral (spectroscopic) reflectance was measured by a spectroscopic photometer for determination of transparency. The measurement method is as described above. As equipment for measurement, a spectroscopic photometer SZ-Σ90 manufactured by NIPPON DENSHI KK was used.

For comparison, sericite superior in transparency and aesthetic feel, and hence used extensively as a powder product was used as a control substance. The results are shown in FIGS. 1(a) and 1(b). When the powder is directly applied to the skin (see FIG. 1(a)), a pattern highly similar to the spectroscopic (spectral) reflected (reflection) curve of the skin is exhibited in case of coating of the inventive substance (Example 1), whilst the reflectance is slightly higher in the wavelength range of 400 to 600 nm, with the transparency (transparent feeling) being high and thereby creating an effect of making the skin look brighter. Conversely, in coating sericite, the reflectance is generally high such that relatively whiteness is felt strongly, with the spectroscopic curve slightly differing from the spectroscopic curve of the skin. If the emulsion is coated on the underlying ground (see FIG. 1(b) approximately the same spectroscopic curve is displayed with the same reflectance as the skin, with the spectroscopic reflection being the same as that of the surface of skin to demonstrate the effect of the appearance of the skin itself, that is, the minute texture of the skin.

(5) Measurement of the Coefficient of Dynamic Friction
Dynamic Frictional Coefficient The measurement method is the same as described above. As the equipment for measurement, a friction sensory tester KES-SE manufactured by KATOTEC KK was used. As samples, the inventive substance (Example 1), sericite used as a base substance in the Example 1, mica having substantially the same chemical composition as sericite in being the same material type as the sericite, and two sorts of composite materials in consideration that the inventive substance is the composite material, were selected for measurement.

The results are shown in the following Table 4. The inventive substance is slightly higher than sericite in the coefficient of dynamic friction (dynamic frictional coefficient), with the difference being extremely small, with the slipperiness being substantially the same. Conversely, the mica or the composite powders are higher than the inventive substance (Example 1) in the coefficient of dynamic friction and are clearly worse in the slipperiness. In the coefficient of dynamic friction (the dynamic frictional coefficient), the inventive substance is approximately equivalent to sericite which is used in large amount as a general filler and which is superior in aesthetic feel, however, in spite of composite material, in distinction from the functional composite material in extensive use in general, it may be estimated enough that the aesthetic feel is not lost if the inventive substance is mixed in large amount into the cosmetics.

TABLE 4

| samples | MIU × $10^{-1}$ |
|---|---|
| inventive substance | 2.23 |
| sericite | 2.18 |
| mica | 2.85 |
| Composite powder (A)*[1] | 3.30 |
| Composite powder (B)*[2] | 2.96 |

*[1]sericite coated with aluminum hydroxide
*[2]sericite coated with titanium dioxide (6) Antibacterial Power Test and Test Result
Test Schematics To a liquid culture medium, admixed with the specimen having an arbitrary concentration, a bacterial solution of *Escherichia coli* or *Staphylococcus aureus* was added. After the liquid culture medium was cultivated under a shaking condition at 35° C. for 18 to 24 hours, the growth or existence of bacteria was checked. The results are shown in Table 5.
1. Test Method
1) Test Bacteria

*Escherichia coli* IFO (*Escherichia coli*)
*Staphylococcus aureus* IFO 13276 (*Staphylococcus aureus*)

2) Culture Medium for Test
   MHB culture medium: Mueller Hinton Broth [DIFCO LABORATORIES INCORPORATED]
   SCDLPA culture medium: SCDLP agar culture medium manufactured by NIPPON SEIYAKU KK]
3) Preparation of Bacterial Solution for Inoculation Test bacteria cultivated over plural generations were inoculated on a MHB culture medium. After cultivation at 35° C. for 18 to 20 hours, the culture was diluted on the MHB culture medium so that the number of bacteria will be approximately $10^4$/ml for use as a bacterial solution for inoculation.
4) Preparation of Culture Medium for Measuring the Sensitivity After the specimen was sterilized under dry heating (at 180° C. for 60 minutes), a 10.5 and a 4 W/V % of liquid suspensions of the specimen were prepared using the MHB culture medium. Moreover, as the 4 W/V % of liquid suspension was agitated sufficiently, the liquid suspension was sequentially diluted on the MHB culture medium by a factor of two to prepare a dual stage diluted liquid of the specimen. 10 ml each of the prepared liquid suspension and each diluted solution were charged into plural L-shaped test tubes for using as a sensitivity measuring culture medium.
5) Cultivation 0.1 ml of a bacterial solution for inoculation was inoculated on sensitivity measurement culture medium and cultivated under a shaking condition at 35° C. for 18 to 24 hours.
6) Judgment With respect to the culture medium for measuring the sensitivity of the present test, the growth or existence of bacteria by observation was not possible to judge due to turbidity caused by addition of the specimen. So, a viable count (the number of live bacteria) of the culture medium for measuring the sensitivity was measured after the end of cultivation (SCDLPA culture medium, 35° C. for two days) and the cases of the number of bacteria per 1 ml of not larger than 106 and larger than 106 were judged to be the case of "growth of bacteria not being recognized" and the case of "growth of bacteria being recognized", respectively.

TABLE 5

Growth or existence of Test Bacteria in Culture Medium Added to Specimen*

| test bacteria | concentration of specimens added (%) | | | | | | | |
|---|---|---|---|---|---|---|---|---|
| | 0.125 | 0.25 | 0.5 | 1 | 2 | 4 | 5 | 10 |
| *Escherichia coli* | + | + | + | − | − | − | − | − |
| *Staphylococcus aureus* | + | − | − | − | − | − | − | − |

Figure 2:
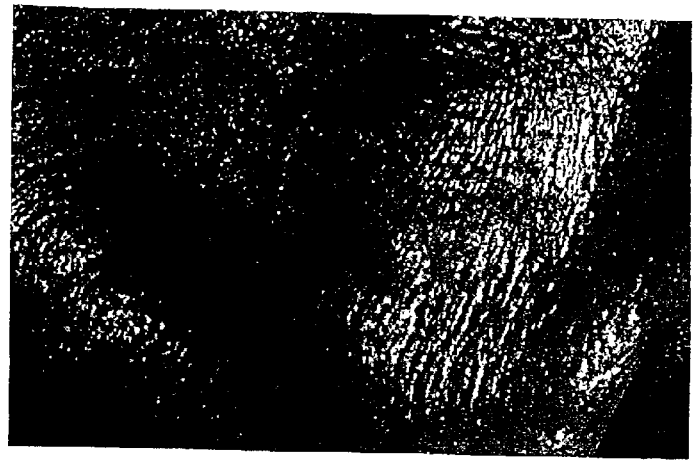
FIG. 2
Figure 2:
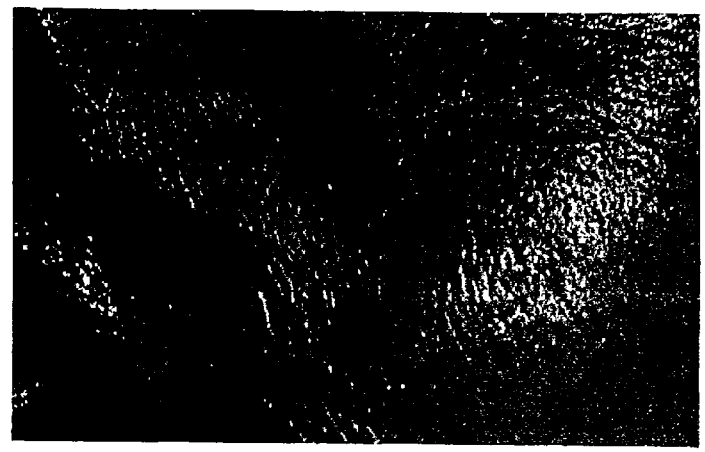
Figure 3:
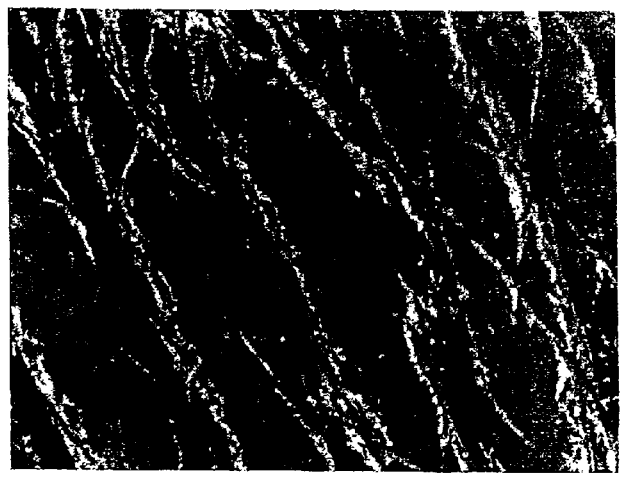
FIG. 3
Figure 3:

−: growth of bacteria not being recognized
+: growth of bacteria being recognized
*shaking culture at 35° C. for 18 to 24 hours (7) Comparison of Cosmetic Effect with Use The result of the comparison of the skin coated with powder (inventive substance; Example 1) and the uncoated skin was evaluated after 5 hours by photographing and video microscope. The results of evaluation are shown in FIGS. 2 and 3. The result of comparison by photographing indicated that the face with a glare clearly in case of an uncoated face (see FIG. 2(*a*)), whereas such "shine" was reduced appreciably in case of coating of the inventive substance (see FIG. 2(*b*)). On the other hand, the result (see FIG. 3) of comparison by video microscope indicated that the sebum was seen to have been collected at the near point from the skin wrinkle grooves and glared in case of an uncoated face (see FIG. 3(*a*)), whereas the powder was seen to have adhered evenly to the skin surface (the surface of skin) while no degradation of the makeup from coming off was observed, in case of coating of the inventive substance (see FIG. 3(*b*)), thus indicating that the inventive substance demonstrates a superior cosmetic effect.
(8) Deodorant Effect Test and Test Result
Samples As a specimen, powder prepared in Example 1 was used. For comparison, sericite (mean particle size: 8 μm; plate-like shape) was used as control specimen.
Deodorant Components The deodorant effect was tested for ammonia, acetic acid and mercaptan.
Test Schematics Each 1 g of a specimen and a control specimen were charged each into an odor bag into which 3 liters of air were charged and were sealed, and subsequently ammonia was added to prepare a gas concentration of approximately 500 ppm. The gas concentration in the bag was measured chronologically. Similar tests were conducted for acetic acid (approximately 50 ppm) and methyl mercaptan (approximately 50 ppm).
1. Reagents and Tools An odor bag manufactured by MIYAKO VINYL KAKO-SHO LTD., ammonia water (28%, special grade) manufactured by KOMUNE KAGAKU YAKUHIN KK, acetic acid (special grade) manufactured by KOMUNE KAGAKU YAKUHIN KK, a gas evolved on adding dilute sulfuric acid to a methyl mercaptan sodium solution (15%), as methyl mercaptan and a gas detecting tube manufactured by GAS TEC KK., were used.

2. Operations

As samples, each 1 g of a specimen and a control specimen was each charged into an odor bag (25 cm×40 cm) and the bag was heat-sealed. Subsequently, 3 liters of air were charged and were sealed into the bag and ammonia was added to prepare a gas concentration of approximately 500 ppm. The samples, so prepared, were allowed to stand under room temperature and the gas concentration in each bag was measured by a gas detecting tube in 0.5, 1, 3, 6 and 24 hours thereafter. As for acetic acid (approximately 50 ppm) and methyl mercaptan (approximately 50 ppm), similar tests were conducted with the measurement time of 2, 5 and 10 minutes and with the measurement time of 10 minutes, respectively. Similar tests were also conducted without charging samples (no sample) by way of a void test.

Test Result

Tables 6 to 8 indicate test results on ammonia, acetic acid and methyl mercaptan.

TABLE 6 ammonia (unit: ppm)

| samples | time elapsed (hours) | | | | |
|---|---|---|---|---|---|
| | 0.5 | 1 | 3 | 6 | 24 |
| Example 1 | 160 | 160 | 130 | 110 | 80 |
| Control | 350 | 350 | 310 | 290 | 180 |
| Void | 490 | 490 | 450 | 410 | 300 |

By way of the initial condition, the gas concentration was prepared to approximately 500 ppm.

TABLE 7 acetic acid (unit: ppm)

| samples | time elapsed (minutes) | | |
|---|---|---|---|
| | 2 | 5 | 10 |
| Example 1 | 2 | 1 | <1 |
| Control | 7 | 7 | 7 |
| Void | 50 | 50 | 50 |

By way of the initial condition, the gas concentration was prepared to approximately 50 ppm.

TABLE 8 methyl mercaptan (unit: ppm)

| samples | time elapsed (minutes) 10 |
|---|---|
| Example 1 | <10 |
| Control | 50 |
| Void | 50 |

By way of the initial condition, the gas concentration was prepared to approximately 50 ppm.

From the results of the above tables 6 to 8, it may be seen that the inventive powder exhibits superior deodorant effects, in particular, that the inventive powder exhibits superior effects of deodorizing the emission of disagreeable odor, that is, a body odor (unusual body odor components).

Example 3

Preparation of Powder Foundation

A powder foundation having the following composition was prepared.

Foundation Composition

| components | parts by weight |
|---|---|
| powders | |
| talc treated with silicone | 8.38 |
| sericite treated with silicone | 21.24 |
| inventive substance (Example 1) | 19.76 |
| mica treated with silicone | 7.00 |
| titanium dioxide treated with silicone | 12.00 |
| polyethylene powder | 13.00 |
| methyl paraben | 0.20 |
| red iron oxide treated with silicone | 1.37 |
| yellow iron oxide treated with silicone | 3.29 |
| ultramarine blue treated with silicone | 0.32 |
| iron black treated with silicone | 0.12 |
| oily agents | |
| glycerine tri-2-ethyl hexanoate | 3.00 |
| squalane | 1.50 |
| nonionic surfactant | 0.30 |
| d-δ-tocopherol | 0.02 |
| methyl polysiloxane* | 8.50 |

*20 centistokes

Preparation Method

The powder components were mixed for three minutes in a Henschel mixer and taken out. Subsequently, the mixture so taken out was pulverized using a screen with a diameter of 0.5 m/mp. This resultant pulverized mixture was charged into a Henschel mixer and added to with oily agents for coating. Using a Herringbone screen of 1.0 m/m, the mixture was powdered by a pulverizer. After this pulverized mixture was charged into a metal mold, it was pressure molded to obtain a powder foundation.

Example 4

Amount of Adsorption of Oleic Acid and Amount of Adsorption of Artificial Sebum

In the powder foundation, obtained in aforementioned Example 3, the amount of adsorption of oleic acid and the amount of adsorption of artificial sebum were measured and compared to conventional products (prior substances). The results are shown in Table 9.

TABLE 9

| samples | amount of adsorption of oleic acid (mg/g) | amount of adsorption of artificial sebum (mg/g) |
|---|---|---|
| inventive substance (Example 3) | 127.5 | 126.3 |
| Conventional product (prior substance) (A) | 77.2 | 54.5 |
| Conventional product (prior substance) (B) | 289.7 | 70.4 |
| Conventional product (prior substance) (C) | 66.9 | 63.9 |

TABLE 9-continued

| samples | amount of adsorption of oleic acid (mg/g) | amount of adsorption of artificial sebum (mg/g) |
|---|---|---|
| Conventional product (prior substance) (D) | 86.6 | 96.6 |

The inventive substance (Example 3) only exhibited high values of the amounts of adsorption of both oleic acid and the artificial sebum. The conventional product (prior substance) (B) and the inventive substance exhibited specifically a selective adsorption for free fatty acids. It may also be seen that the inventive substance exhibited adsorbent effects for a mixed system of a variety of substances, such a triglycerides, diglycerides, free fatty acids, squalene and the like, such as artificial sebum, which are apparently superior to those of the conventional products.

Example 5

Evaluation of Usability

The powder foundation obtained in Example 3 was evaluated. As a control substance (Comparative Example 1), a powder foundation prepared in accordance with Example 3 except substituting a sericite treated with silicone for all of the powder of Example 1 was used. For evaluation method, six expert peoples in a panel actually used the powder foundation and, after use, five-stage evaluation was conducted as to the following evaluation items in accordance with the following standard:

Evaluation Standard (Evaluation standard)

| | 1 | 2 | 3 | 4 | 5 |
|---|---|---|---|---|---|
| long wear | bad | | ⇔ | | good |
| transparency | no | | ⇔ | | yes |
| extension on skin | bad | | ⇔ | | good |
| makeup finish | not beautiful | | ⇔ | | beautiful |
| affixture | no | | ⇔ | | yes |
| adhesion | bad | | ⇔ | | good |

(Result of Evaluation)

| items of evaluation | Example 3 | Comparative Example 1 |
|---|---|---|
| long wear | 4.9 | 1.1 |
| transparency | 4.2 | 2.2 |
| extension on skin | 3.6 | 3.6 |
| makeup finish | 4.8 | 2.7 |
| affixture | 4.6 | 2.6 |
| adhesion | 4.5 | 3.8 |

Example 6

Evaluation of Long Wear for Makeup by Photographing and the Like

The long wear for makeup was evaluated on the powder foundation of the inventive substance (Example 3) by photographing and by the use of a video microscope.

Figure 4:
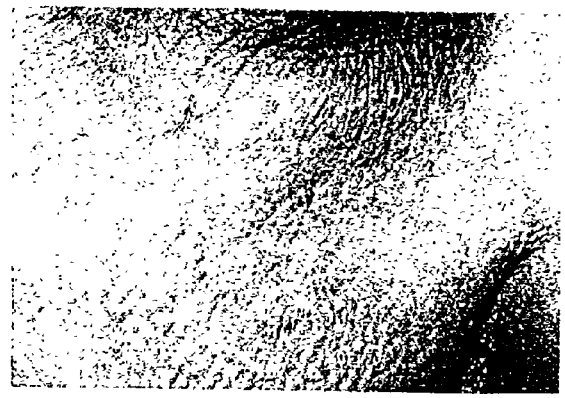
FIG. 4
Figure 4:
Figure 4:
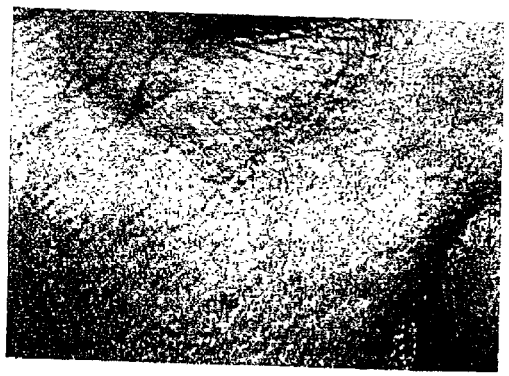
Figure 4:
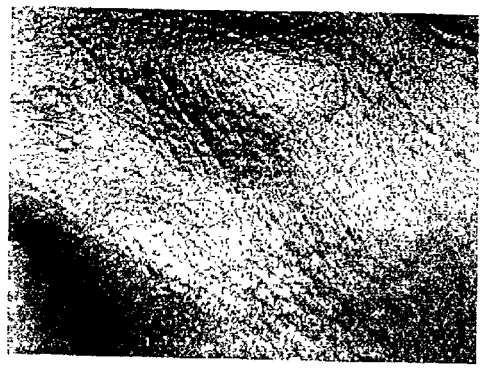
Figure 4:
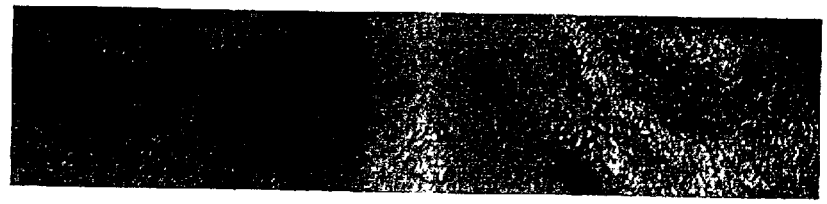

(1) The powder foundation was coated on a face, and the appearance of long wear for makeup after lapse of five hours was photographed using a digital camera. FIG. 4 shows the result of comparison to the powder foundation of the Comparative Example 1 (without using the inventive powder) prepared in Example 5.

It is seen from these results that the makeup by the product of Comparative Example 1 (FIG. 4(b) and FIG. 4(c)) indicated "shine" due to sebum not only at a site near the window but also under the light, whereas the inventive substance looks natural thus understanding to be superior in long wear for makeup.

Figure 5:
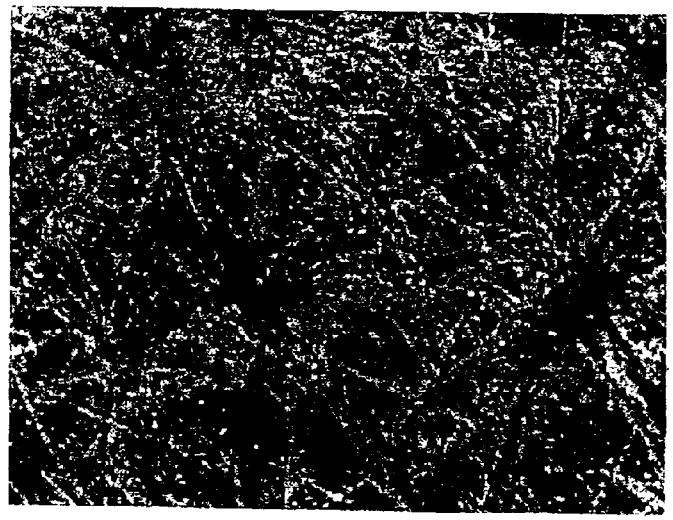
FIG. 5
Figure 5:
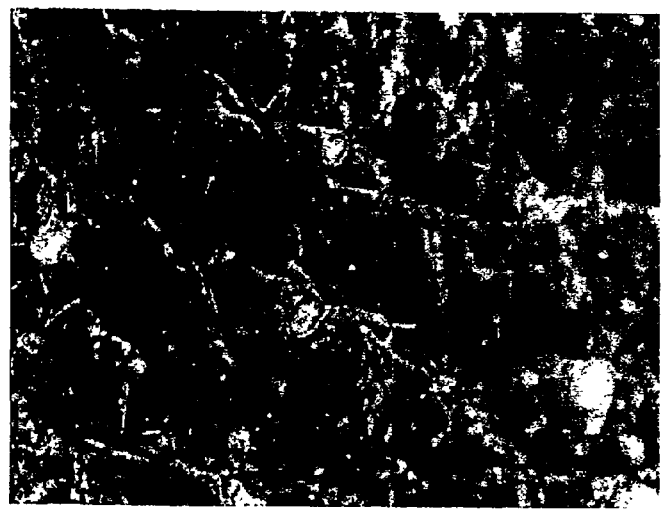

(2) The powder foundation was coated on the face and the appearance of the long wear for makeup after lapse of five hours was photographed with a video microscope with a magnification factor of ×200. FIG. 5 shows the result of comparison with the powder foundation of the aforementioned Comparative Example 1.

These results indicated to the superior long wear of the inventive substance for makeup. That is, it may be seen that, with respect to the makeup by the inventive substance, the powder are adhered neatly to the skin surface (the surface of skin) even after lapse of five hours, whereas, with respect to the control substance, the cause of the makeup to come off takes place significantly by the sebum, where the powder does not exist on the top of the wrinkle on the skin and descending into the skin wrinkle grooves. Moreover, "shine" by the sebum is also seen.

Example 7

Under-makeup Emulsion

An under-makeup emulsion was prepared by the following composition:

| components | parts by weight |
|---|---|
| oily phase | |
| squalane | 4.0 |
| cetyl octanoate | 5.5 |
| jojoba oil | 1.5 |
| cetanol | 0.6 |
| d-δ-tocopherol | 0.02 |
| glycerine monooleate | 0.2 |
| glycerine monostearate | 0.5 |
| P.O.E. behenyl ether | 1.6 |
| aqueous phase | |
| carboxy vinyl polymer | 0.15 |
| glycerine | 17.0 |
| methyl paraben | 0.3 |
| xanthane gum | 0.05 |
| potassium hydroxide | 0.09 |
| inventive substance (Example 1) | 5.0 |
| purified water | 63.49 |

Preparation Method

The components of the oily phase were dissolved homogeneously at 80° C. A mixture of aqueous phase components, in which the inventive substance (powder of Example 1) was dispersed homogeneously, was heated to 80° C. and added to the homogeneously dissolved oily components and emulsified at 80° C. The mixture was cooled to 50° C. after storage for ten minutes at 80° C., and an under-makeup emulsion was obtained.

Evaluation of Usability (1) Samples

As a control substance (Comparative Example 2), an under-makeup emulsion, prepared in accordance with the Example 7 except substituting the purified water for the powder of the inventive substance (Example 1) among the aqueous phase components used in the composition of Example 7, was used.

(2) Method of Use

The under-makeup emulsion was evaluated based on comparison of the case of using the powder foundation prepared in Comparative Example 1 with the under-makeup emulsion prepared in the present Example 7 and the case of using the powder foundation prepared in Comparative Example 1 with the control substance prepared in Comparative Example 2 (under-makeup emulsion).

(3) Results of Evaluation

As for the method for evaluation, the five-stage evaluation was also performed in accordance with the aforementioned Example 5. The results were shown in Table 10. It may be seen from these results that the inventive substance has superior properties.

TABLE 10

| items of evaluation | Example 7 | Comparative Example 2 |
| --- | --- | --- |
| long wear | 4.5 | 1.0 |
| transparency | 4.0 | 2.1 |
| extension on skin | 3.6 | 3.2 |
| makeup finish | 4.3 | 2.5 |
| affixture | 4.2 | 2.3 |
| adhesion | 4.0 | 3.0 |

Example 8

Preparation of Emulsified Foundation

An emulsified foundation was prepared in accordance with the following composition;

| components | parts by weight |
| --- | --- |
| oily phase | |
| stearic acid | 0.75 |
| glycerine monostearate | 3.0 |
| polyethylene glycol monostearate | 0.5 |
| P.O.E. sorbitan monostearate | 1.5 |
| glycerine tri-2-ethyl hexanoate | 3.0 |
| sorbitan sesquioleate | 0.3 |
| titanium dioxide | 5.0 |
| squalane | 2.0 |
| cetyl octanoate | 8.2 |
| talc | 4.0 |
| red iron oxide | 0.3 |
| yellow iron oxide | 0.9 |
| purple iron oxide | 0.3 |
| aqueous phase | |
| polyethylene glycol 200 | 10.0 |
| carboxymethyl cellulose sodium | 0.1 |
| xanthane gum | 0.05 |
| methyl paraben | 0.3 |

-continued

| components | parts by weight |
| --- | --- |
| triethanolamine | 0.7 |
| magnesium aluminum silicate | 1.0 |
| inventive substance (Example 1) | 10.0 |
| purified water | 48.1 |

Preparation Method

Of the oily components, talc, titanium dioxide and organic pigments were homogeneously dispersed to give a mixture of the oily phase, which was heated to 85° C. On the other hand, the mixture of the aqueous phase components, obtained on homogeneously dispersing the inventive substance and magnesium aluminum silicate in the aqueous phase, was heated to 85° C. as was the oily phase mixture. The aqueous phase then was added to the oily phase dispersion of 85° C. prepared as described above and emulsified. After the end of the emulsification, the emulsion was held at 85° C. for 15 minutes and cooled up to 30° C. to produce an emulsion type foundation.

Evaluation of Usability (1) Samples

As a control substance (Comparative Example 3), an emulsified foundation prepared in the same way as in Example 8 except substituting the purified water for the inventive substance in the aqueous phase in the Example 8 was used.

(2) Method of Use

The control substance and the inventive substance were used by nine aesthetic persons in the panel alternately every other day for two weeks. The evaluation was based on the results obtained.

(3) Results of Evaluation

The evaluation was also performed in five stages as in the Example 5 described above. Table 11 shows the results, from which it is seen that the inventive substance exhibits superior properties.

TABLE 11

| items of evaluation | Example 8 | Comparative Example 3 |
| --- | --- | --- |
| long wear | 4.6 | 1.2 |
| transparency | 4.3 | 2.4 |
| extension on skin | 3.7 | 3.7 |
| makeup finish | 4.5 | 2.6 |
| affixture | 4.4 | 2.5 |
| adhesion | 4.1 | 2.9 |

Example 9

Preparation of Body Deodorant

A body deodorant was prepared based on the following composition:

Composition of the Body Deodorant

| components No. | components | parts by weight |
|---|---|---|
| 1 | talc treated with silicone | 38.0 |
| 2 | inventive substance (Example 1) | 40.0 |
| 3 | cyclic dimethyl polysiloxane | 20.0 |
| 4 | cetyl octanoate | 1.0 |
| 5 | glycerine tri-2-ethyl hexanoate | 1.0 |

Preparation Method

The components 1 and 2 were mixed in a Henschel mixer and powdered by a pulverizer. The pulverized mass was transferred to a Henschel mixer and added to with a liquid mixture of the components 3 to 5 as the oily components for mixing. The resultant mixture then was powdered by a pulverizer to prepare a body deodorant.

Evaluation

A deodorant test then was conducted for evaluating the body deodorant produced.

Deodorant Testing Method

Eight healthy male persons in the panel who were recognized as suffering from strong foot smell were selected for member of a panel in the evaluation and put to the test on the aforementioned body deodorant (inventive substance) admixed with the composite material prepared in Example 1. The state in which a person in the member wears a stocking and a shoe and is heated and stuffed for three hours is termed the "pre-using" state, and a functional test was conducted on the degree of foot smell at this time. The body deodorant was then coated on the foot and the person in the panel then wears a stocking and a shoe and kept in this state for 30 minutes to five hours. After this time interval, the degree of foot smell was similarly evaluated. The test was carried out for four days every day to find an average value.

Standard for Evaluation

The degree of foot smell was evaluated in seven stages of 0 to 6 based on the following seven standards to find average values (scores) of the results of the eight persons in the panel.

0: none
1: very slight smell
2: slight smell
3: some noticeable smell
4: noticeable smell
5: strong smell
6: very strong smell.

The results are shown in the following Table 12:

TABLE 12

| time elapsed (after coating of the inventive substance) | scores |
|---|---|
| 30 minutes | 0 |
| 1 hour | 0 |
| 2 hours | 0.4 |
| 3 hours | 0.9 |
| 4 hours | 2.0 |
| 5 hours | 2.8 |
| "before use" (control) | 5.1 |

From the above test results, it may be seen that the body deodorant of the inventive substance (present invention) has a superior deodorant effect.

Effect of Invention

The present invention provides a powder which specifically adsorbs free fatty acids, in particular unsaturated fatty acids, adsorbs and solidifies the sebum secreted, forms a solid film so as not to obstruct skin physiology, has the same light reflection curve as that from the skin surface and the skin feeling and which is superior in long wear effect for makeup and antibacterial effect, and which may be conveniently used for cosmetics. The present invention also provides a cosmetics and a sebum-adsorbent having these superior effects by the use of these powders. Moreover, the powder in the present invention exhibits the operation of adsorbing, solidifying, or congealing the body odor components and hence the present invention also provides a body deodorant employing the inventive powder.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items might fall under the modifications aforementioned.

What is claimed is:

1. A three layered coated powder composition, comprising:
 a cured coated core, comprising:
  a core substance comprising a powder for use in cosmetics;
  a hydroxy apatite "heat-treating" layer provided on the surface of said core substance to produce a coated core, said coated core being to produce a coated core; and
 a zinc oxide layer fixed to said hydroxy apatite layer of said cured coated core, to produce said three layered coated powder cosmetic composition.

2. A cosmetic composition comprising the three layer coated powder composition of claim 1.

3. The three layered coated powder composition of claim 1, wherein said three layered coated powder composition adsorbs sebum.

4. The three layered coated powder composition of claim 1, said core substance comprising:
 an inorganic powder and optionally an organic powder; and
 one or more members selected from the group consisting of a clay mineral, a synthetic clay mineral, a metal hydroxide, and a metal oxide.

5. The three layered coated powder composition of claim 1, said zinc oxide comprising a low crystalline zinc oxide and/or an amorphous zinc oxide.

6. The three layered coated powder composition of claim 1, said zinc oxide having a crystalline size of 1000 Å in length, as obtained from Scherrer's equation.

7. The three layered coated powder composition of claim 1, wherein said core substance comprises a scale, a plate, a lamella, or a bar shape.

8. The three layered coated powder composition of claim 1, said core substance having a mean particle size of 0.1 to 600 μm and said zinc oxide having a mean particle size of 0.01 to 1 μm.

9. The three layered coated powder composition of claim 1, said hydroxyapatite is present in an amount of from 2 to 50 wt %, and said zinc oxide is present in an amount of from 2 to 8 wt %, based on total weight of said three layered coated powder composition.

10. A sebum-adsorbent composition comprising the three layered coated powder composition as defined in claim 3.

11. A body deodorant composition comprising the three layered coated powder composition as defined in any one of claims 1 to 3.

12. A cosmetic composition comprising the three layered coated powder composition as defined in any one of claim 2 or 3.

* * * * *